United States Patent [19]

Sanchez et al.

[11] Patent Number: 5,451,654

[45] Date of Patent: Sep. 19, 1995

[54] HYDROXY-PEROXIDES AND THEIR USES

[75] Inventors: Jose Sanchez, Grand Island; Arthur L. Baron, Getzville, both of N.Y.

[73] Assignee: Elf Atochem North America, Inc., Philadelphia, Pa.

[21] Appl. No.: 344,310

[22] Filed: Nov. 22, 1994

Related U.S. Application Data

[60] Division of Ser. No. 205,273, Mar. 2, 1994, Pat. No. 5,387,654, which is a division of Ser. No. 1,921, Jan. 8, 1993, Pat. No. 5,304,649, which is a continuation of Ser. No. 528,265, May 23, 1990, abandoned, which is a continuation of Ser. No. 303,415, Jan. 30, 1989, abandoned.

[51] Int. Cl.$^6$ ............................................. C08F 2/00
[52] U.S. Cl. ..................................... 526/204; 526/212
[58] Field of Search ................................ 526/204, 212

[56]  References Cited

U.S. PATENT DOCUMENTS

| | | |
|---|---|---|
| 3,236,872 | 2/1966 | Manly et al. . |
| 3,326,859 | 6/1967 | Seiner .................... 558/263 |
| 3,576,826 | 4/1971 | Bafford et al. . |
| 3,660,468 | 5/1972 | McKellin . |
| 3,671,651 | 6/1972 | D'Angelo . |
| 3,725,455 | 4/1973 | D'Angelo et al. ............. 260/463 |
| 3,743,630 | 7/1973 | Wood ........................... 560/302 |
| 3,952,041 | 4/1976 | D'Angelo et al. . |
| 3,991,085 | 11/1976 | Abma et al. . |
| 4,115,455 | 9/1978 | McKellin et al. . |
| 4,119,657 | 10/1978 | Komai et al. .............. 558/263 |
| 4,180,518 | 12/1979 | Mageli et al. . |
| 4,525,308 | 6/1985 | Sanchez . |
| 4,634,753 | 1/1987 | Sanchez ..................... 526/216 |
| 5,304,649 | 4/1994 | Sanchez et al. . |
| 5,387,654 | 2/1995 | Sanchez et al. . |

OTHER PUBLICATIONS

"Suggested SPI Procedure, Procedure for Running Exotherm Curves-Using the Thermocouple Needle'-'-24th Ann. Tech. Conf., 1969, Reinforced Plastics/Composites Division, The Society of the Plastic Industry, Inc.

"Suggested SPI Procedure, 25° C. Get Time-Polyester Resin" 24th Ann. Tech. Conf., 1969, Reinforced Plastics/Composite Division, The Society of the Plastics Industry, Inc.

*Primary Examiner*—Joseph L. Schofer
*Assistant Examiner*—N. Sarofim
*Attorney, Agent, or Firm*—Royal E. Bright

[57]  ABSTRACT

Novel hydroxy peroxides of the Structure A $$HO-R_{11}-X-OO-R \qquad (A)$$

[wherein R—, —$R_{11}$— and —X— are as defined in the Summary of the Invention Section], having 10 hour half-life temperatures of 85°–100° C., the processes for their preparation, and the use of these novel compositions in curing of unsaturated polyester resins and in initiating polymerization of ethylenically unsaturated monomers.

2 Claims, No Drawings

HYDROXY-PEROXIDES AND THEIR USES

This is a continuation divisional of application Ser. No. 08/205,273 filed on Mar. 2, 1994, now U.S. Pat. No. 5,397,654 which is a divisional of application Ser. No. 08/001,921, Jan. 8, 1993 now U.S. Pat. No. 5,304,649 which was a continuation of application Ser. No. 528,265, May 23, 1990, abandoned, which is a continuation of Ser. No. 303,415, Jan. 30, 1989 abandoned.

BACKGROUND OF THE INVENTION

This invention relates to novel hydroxy-peroxides of the Structure A:

$$HO-R_{11}-X-OO-R \qquad (A)$$

[wherein R—, —$R_{11}$— and —X— are as defined in the Summary of the Invention Section] having 10 hour half-life temperatures of 85°–110° C., the processes for their preparation, and the use of these novel compositions in curing of unsaturated polyester resins and in initiating polymerization of ethylenically unsaturated monomers.

PRIOR ART

In applicant's opinion, the closest prior art to this invention includes U.S. Pat. No. 3,236,872 which discloses hydroxy-peroxides of the structure:

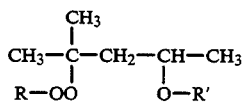

(wherein R— is hydrogen, an acyl, an aroyl or alkyl group, especially the t-butyl group, t-amyl or the hexylene glycol residue; R'— is hydrogen or an acyl, aroyl or alkyl group.)

The only acyl or aroyl groups specifically illustrated were acetyl and benzoyl. Additional close prior art includes U.S. Pat. Nos 4,525,308 and 4,634,753 which disclose hydroxy-peroxyesters having 10 hour half-life temperatures below about 75° C. This art does not cover the compositions of the present invention which have 10 hour half-life temperatures of 85°–110° C.

U.S. Pat. No. 3,671,651 (col 8, lines 1 and 2) discloses a hydroxy-peroxyester, t-butyl peroxy-(3-hydroxypropionate). U.S. Pat. No. 4,115,455 discloses the preparation of hydroxy-dialkyl peroxides by means of either catalytic hydrogenation of carbonyl-containing peroxides or by treatment of carbonyl-containing peroxides with an alkali aluminum hydride or an alkali boron hydride. U.S. Pat. No. 3,576,826 discloses processes for preparing ether-peroxy compounds by the uncatalyzed addition of t-alkyl hydroperoxides to alpha-substituted vinyl ethers. U.S. Pat. No. 4,180,518 discloses monoperoxycarbonates and peroxycarbamates of the structure

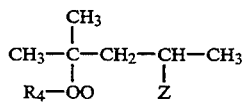

where $R_4$— is t-alkyl of 4 to 10 carbons, t-aralkyl of 9–16 carbons, t-cycloalkyl of 6 to 12 carbons,

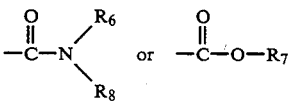

and Z— is

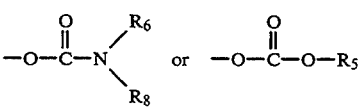

The hydroxy-monoperoxycarbonates of the instant invention are not disclosed by U.S. Pat. No. 4,180,518 since this patent does not disclose that Z— is HO—.

The novel hydroxy-peroxides of the instant invention possess reactive hydroxy functions in addition to the peroxide functions. Peroxides with reactive functional groups are known in the literature and several are sold commercially. Commercially produced peroxides with reactive functional groups include succinic acid peroxide (carboxy groups) and OO-t-butyl O-hydrogen monoperoxymaleate (carboxy group). More recently, 3-hydroxy-1,1-dimethylbutyl peroxy-2-ethylhexanoate (hydroxy group) and 3-hydroxy-1,1-dimethylbutyl peroxyneoheptanoate (hydroxy group) have been offered commercially. Other reactive initiators are disclosed in the literature. U.S. Pat. No. 3,236,872 discloses hydroxy-hydroperoxides and hydroxy-dialkyl peroxides, U.S. Pat. No. 3,991,085 discloses epoxy-peroxides, U.S. Pat. Nos. 3,660,468, 3,671,651 and 3,952,041 disclose peroxides with reactive acid chloride, chloroformate, anhydride and/or carboxy groups. Such functionalized initiators enable polymer producers to enhance the utility and value of polymers by allowing them to 'put' the reactive groups onto polymers by means of free-radical polymerization of ethylenically unsaturated monomers or by means of grafting reactions using these reactive peroxide initiators.

Thus, there is a need in the polymer industry for reactive functionalized initiators (peroxides and azos) which can be used to produce reactive, functionalized polymers or peroxy-polymers by various means such as free-radical polymerization of ethylenically unsaturated monomers, grafting onto polymers, chain termination of condensation polymers, reaction with co-functionalized polymers, etc. When the initiator group of the functionalized initiator decomposes in these processes, polymers with functional groups (i.e., at chain ends or pendant) are produced. Such polymers can be chain extended to produce desirable high performance polymers. This technique is the basis for the high solids acrylic coatings business in which hydroxy-containing low molecular weight acrylic copolymers are chain extended/cross linked with co-reactive compounds after being applied in automotive coatings applications. When the reactive functional initiator is used to chain terminate condensation polymers or to react with co-reactive polymers, polymers with initiator end groups and/or pendant initiator groups are produced. These peroxy-polymers can then be used to produce block or graft copolymers that can be used in compatibilizing polymer blends and alloys produced from incompatible polymers. Hydroxy-peroxides have utility in the above applications.

There are a number of hydroxy-peroxides described in the art. U.S. Pat. Nos. 4,525,308 and 4,634,753 describe and disclose hydroxy-peroxyesters having 10 hour half-life temperatures (i.e., the temperature at which the half-life of the initiator is 10 hours) below 75° C. These peroxides find use in vinyl chloride polymerizations and copolymerizations and in lower temperature ethylene polymerizations and copolymerizations. U.S. Pat. No. 3,236,872 discloses hydroxy-hydroperoxides and hydroxy-dialkyl peroxides which have 10 hour half-life temperatures above about 120° C. These peroxides find use in higher temperature applications such as polyethylene crosslinking and polypropylene modification. There is a need in the polymer industry for hydroxy-initiators which have 10 hour half-life temperatures between 75° C. and 120° C. for use in preparing polystyrenes, polyacrylates and other polymers with hydroxy end groups for subsequent reactions. U.S. Pat. No. 3,671,651 discloses a hydroxy-peroxyester, t-butyl peroxy-3-hydroxypropionate, which is estimated to have a 10 hour half-life temperature of about 100° C., right in the middle of the desirable temperature range of 75° C. to 120° C.. However, the product is difficult to prepare and the substrate employed in its synthesis, beta-propiolactone, is a highly toxic cancer suspect agent. On the other hand, the hydroxy-peroxides of the instant invention have 10 hour half-life temperatures in the desirable 85° C. to 110° C. temperature range, are relatively easy to prepare and are prepared from relatively non-toxic starting materials. Hence, they satisfy a need and advance the polymerization art.

Some of the hydroxy-peroxides of this invention were prepared by reacting hydroxy-hydroperoxides with certain hindered substituted benzoyl halides. This result was unexpected in view of the art, especially U.S. Pat. No. 3,236,872. Claim 1 of U.S. Pat. No. 3,236,872 broadly covers hydroxy-peroxides including hydroxy-peroxyesters. The examples of U.S. Pat. No. 3,236,872 teach that reactions of benzoyl chloride and acetyl chloride with hydroxy-hydroperoxides (such as 3-hydroxy-1,1-dimethylbutyl hydroperoxide) result in acylation at both the hydroxy group as well as at the hydroperoxy group resulting in the formation of a benzoate-peroxybenzoate with benzoyl chloride (Example 3) and an acetate-peroxyacetate with acetyl chloride (Example 6). According to Example 11 of the instant invention, reaction of benzoyl chloride with excess 3-hydroxy-1,1-dimethylbutyl hydroperoxide resulted in formation of 3-benzoyloxy-1,1-dimethylbutyl peroxybenzoate (C-1a) rather than in formation of 3-hydroxy-1,1-dimethylbutyl peroxybenzoate (C-1). Even the skewing of the process conditions in favor of formation of C-1, by employing excess 3-hydroxy-1,1-dimethylbutyl hydroperoxide, failed to result in formation of C-1, but instead, C-1a was formed. Thus, U.S. Pat. No. 3,236,872 does not teach one skilled in the art how to make hydroxy-peroxyesters from 3-hydroxy-1,1-dimethylbutyl hydroperoxide and benzoyl chlorides.

We surprisingly found that, under essentially the same process conditions as employed in Example 11 of the instant invention, hindered benzoyl chlorides, such as 2-chlorobenzoyl chloride, 2-methylbenzoyl chloride, 2-bromobenzoyl chloride and others, resulted in formation of the corresponding hydroxyalkyl substituted-peroxybenzoates (see Compositions I-7, I-8, I-9 and I-10, Examples 7, 8, 9 and 10).

SUMMARY OF THE INVENTION

This invention provides for novel hydroxy-peroxides, having 10 hour half-life temperatures of 85°-110° C., having Structure A:

$$HO-R_{11}-X-OO-R \qquad (A)$$

where —X— can be a direct bond or the diradical,

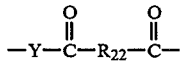

and,

I. when —X— is a direct bond,
R— is selected from the structures,

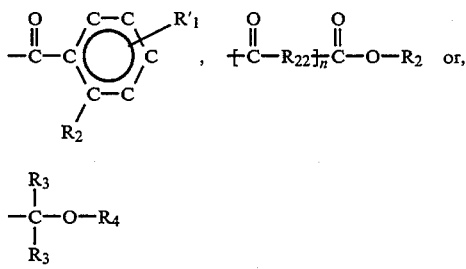

where $R_1$— is a lower alkyl radical of 1 to 4 carbons, an alkoxy radical of 1 to 4 carbons, a phenyl radical, an acyloxy radical of 2 to 8 carbons, a t-alkylperoxycarbonyl radical of 5 to 9 carbons, hydroxy, fluoro, chloro or bromo, $R'_1$— is hydrogen or is selected from the same radicals as $R_1$—, and can be the same as or different than $R_1$—, and, n is 0 or 1, $R_2$— is a substituted or unsubstituted alkyl radical of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6–10 carbons, hydroxy, chloro, bromo or cyano or a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, or $R_2$— can be the radical,

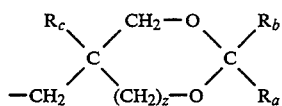

where z is 0 or 1, $R_a$—, $R_b$— and $R_c$— are the same or different and are hydrogen or alkyl radicals of 1 to 8 carbons, with the further proviso that $R_a$ and $R_b$ can be connected forming a substituted or unsubstituted ring containing 5–12 carbons, substituents being one or more alkyl radicals of 1 to 5 carbons or phenyl radicals, —$R_{22}$— is a substituted or unsubstituted alkylene diradical of 2 to 3 carbons, substituents being one or more lower alkyl radicals of 1 to 4 carbons, or a substituted or unsubstituted 1,2-phenylene diradical, substituents being one or more lower alkyl radicals of 1 to 4 carbons, chloro, bromo, nitro or carboxy, and, $R_3$— is a lower alkyl radical of 1 to 4 carbons, and, additionally, the two $R_3$— radicals can be connected together forming a ring containing 5 to 6 carbons, and, $R_4$— is a lower alkyl radical of 1 to 4 carbons, and, the —$R_{11}$— diradical is the structure,

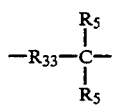

where $R_5$— is a lower alkyl radical of 1 to 4 carbons, and —$R_{33}$— is a substituted or unsubstituted alkylene diradical of 2 to 4 carbons, substituents being one or more lower alkyl radicals of 1 to 4 carbons, and, II. when —X— is the diradical

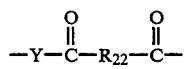

—Y— is —O— or —$NR_6$—, where $R_6$— is hydrogen or a substituted or unsubstituted alkyl radical of 1 to 8 carbons, substituents being one or more lower alkyl radicals of 1 to 4 carbons or hydroxy, and, $R_{22}$— has the same definition as when —X— is a direct bond, and, R— can be a substituted or unsubstituted t-alkyl radical of 4 to 12 carbons, substituents being lower alkyl radicals of 1 to 4 carbons or t-alkylperoxy radicals of 4 to 8 carbons, a t-cycloalkyl radical of 6 to 13 carbons, a t-alkynyl radical of 5 to 8 carbons, or a t-aralkyl radical of 9 to 13 carbons, and, —$R_{11}$— can be a substituted or unsubstituted alkylene diradical of 2 to 8 carbons, optionally possessing one or more oxygen or nitrogen heteroatoms in the alkylene chain, substituents being one or more lower alkyl radicals of 1 to 4 carbons, lower hydroxyalkyl radicals of 1 to 4 carbons or hydroxy.

The invention also provides for novel processes using the novel hydroxy-peroxides of Structure A as curing agents for the curing of unsaturated polyester resin compositions by heating such resins in the presence of initiating amounts of the novel hydroxy-peroxides of Structure A at appropriate temperatures.

The invention still further provides novel processes using the novel hydroxy-peroxides of Structure A as free radical initiators for polymerizing ethylenically unsaturated monomers (such as styrene, ethylene etc.) by the use of initiating amounts of the novel hydroxy-peroxides of Structure A at appropriate temperatures.

DETAILED DESCRIPTION OF THE INVENTION PREPARATIONS OF THE NOVEL HYDROXY-PEROXIDES

The types of novel hydroxy-peroxides of this invention include several types of peroxides when —X— of Structure A is a direct bond. These include hindered hydroxy-peroxyesters, i.e. , where R— is:

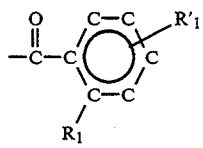

OO-hydroxyalkyl O—alkyl monoperoxydicarboxylates, i.e., where R— is:

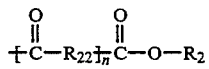

and n is 1, hydroxy-monoperoxycarbonates, i.e., where R— is:

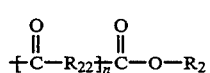

and n is 0, and hydroxy-monoperoxyketals, i.e., where R— is:

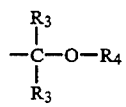

The types of novel hydroxy-peroxides of this invention also include hydroxy-peroxyesters when —X— of Structure A is:

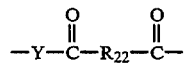

The novel hindered hydroxy-peroxyesters of Structure A can be prepared by reacting acid halides of Structure B (where Q— is Cl— or Br—)

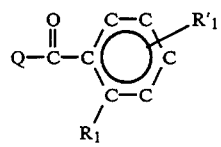

with hydroxy-hydroperoxides of Structure C

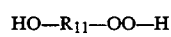

in the presence of an organic or inorganic base. Acid halides of Structure B include, without limiting, 2-methylbenzoyl chloride, 2-ethylbenzoyl chloride, 2-methoxybenzoyl chloride, 2,6-dimethylbenzoyl chloride, 2-phenylbenzoyl chloride, 2-chlorobenzoyl chloride, 2,4-dichlorobenzoyl chloride, 2-bromobenzoyl chloride, 2-bromobenzoyl bromide, 2-fluorobenzoyl chloride, 2-acetoxybenzoyl chloride, and 2-(t-butylperoxycarbonyl)benzoyl chloride.

Non-limiting examples of hydroxy-hydroperoxides of Structure C include 3-hydroxy-1,1-dimethylpropyl hydroperoxide, 3-hydroxy-1,1-dimethylbutyl hydroperoxide and 4-hydroxy-1,1-dimethylbutyl hydroperoxide.

Inorganic bases that are useful in the novel synthetic processes of this invention include sodium hydroxide, sodium carbonate, sodium hydrogen carbonate, potassium hydroxide, potassium carbonate, potassium hydrogen carbonate, calcium hydroxide, barium hydroxide, calcium carbonate and trisodium phosphate. Non-limiting examples of organic bases useful for preparing the hydroxy-peroxides of this invention include trimethylamine, triethylamine, tri-n-butylamine, 1,4-diazabicyclo[2.2.2]octane, pyridine, N,N-dimethylaniline, N,N-diethylaniline, p-N,N-dimethylaminopyridine and methyl-pyridines.

The novel OO-hydroxyalkyl O-alkyl monoperoxydicarboxylates of Structure A can be prepared by reacting an acid halide of Structure D

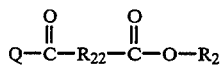
(D)

with a hydroxy-hydroperoxide of Structure C in the presence of an organic or inorganic base. Acid halides of Structure D include 2-methoxycarbonylbenzoyl chloride, 2-n-butoxycarbonylbenzoyl chloride, 2-(2-ethylhexoxycarbonyl)benzoyl chloride, 2-cyclohexoxycarbonylbenzoyl chloride, 2-(4,4-dimethyl-3,5-dioxacyclohexoxycarbonyl)benzoyl chloride, 2-[(1,4,4-trimethyl-3,5-dioxacyclohexyl)methoxycarbonyl]benzoyl chloride, 2-[(3,3-dimethyl-2,4-dioxacyclopentyl)methoxycarbonyl]benzoyl chloride, 2-[(2,4-dioxacyclopentyl)methoxycarbonyl]benzoyl chloride, 3-methoxycarbonylpropionyl chloride, 4-butoxycarbonylbutyryl chloride, 3-(4,4-dimethyl-3,5-dioxacyclohexoxycarbonyl)propionyl chloride, 3-(3,5-dioxacyclohexoxycarbonyl)propionyl chloride, 4-[(1,4,4-trimethyl-3,5-dioxacyclohexyl)methoxycarbonyl]butyryl chloride, 3-[(3,3-dimethyl-2,4-dioxacyclopentyl)methoxycarbonyl]propionyl chloride and 3,4,5,6-tetrachloro-2-methoxycarbonylbenzoyl chloride.

The acid halides of Structures B and D can be prepared by treating the corresponding carboxylic acids with acid halogenating agents such as $PCl_3$, $POCl_5$, $PCl_5$, thionyl chloride, thionyl bromide, phosgene (in the presence of dimethylformamide, DMF), benzotrichloride and others.

The novel hydroxy-monoperoxycarbonates of Structure A can be prepared by reacting alkyl haloformates of structure

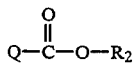
(E)

with hydroxy-hydroperoxides of Structure C in the presence of an organic or inorganic base.

Alkyl haloformates of Structure E include methyl chloroformate, ethyl chloroformate, isopropyl chloroformate, isopropyl bromoformate, butyl chloroformate, 2-butyl chloroformate, neopentyl chloroformate, 2-ethylhexyl chloroformate, 2-ethylbutyl chloroformate, 2-butyloctyl chloroformate, 4-methyl-2-pentyl chloroformate, dodecyl chloroformate, hexadecyl chloroformate, 2-chloroethyl chloroformate, 2-butoxyethyl chloroformate, 2-phenoxyethyl chloroformate, cyclohexyl chloroformate, 4-t-butylcyclohexyl chloroformate, 3,3,5-trimethylcyclohexyl chloroformate, cyclododecyl chloroformate, 2,2,6,6-tetramethyl-4-piperidinyl chloroformate (and hydrochloride salt), 1,2,2,6,6-pentamethyl-4-piperidinyl chloroformate (and hydrochloride salt), (3,3-dimethyl-2,4-dioxacyclopentyl)methyl chloroformate, (2,4-dioxacyclopentyl)methyl chloroformate, (4,4-dimethyl-3,5-dioxacyclohexyl) chloroformate, (3,5-dioxacyclohexyl)chloroformate, (1,4,4-trimethyl-3,5-dioxacyclohexyl)methyl chloroformate and 1,3-dimethyl-3-(t-butylperoxy)butyl chloroformate.

The alkyl haloformates of Structure E can be prepared by reacting the corresponding alcohols with excess phosgene.

The novel hydroxy-monoperoxyketals of this invention can be prepared by reacting alpha-substituted vinyl ethers of Structure F:

(F)

(where $R'_3$— is hydrogen or an alkyl radical of 1 to 3 carbons, and $R_3$— and $R'_3$— can be connected together to form a ring containing 5 to 6 carbons) with hydroxy-hydroperoxides of Structure C in the absence of any catalyst.

Non-limiting examples of alpha-substituted vinyl ethers of Structure F include methyl isopropenyl ether, ethyl isopropenyl ether, n-butyl isopropenyl ether, 1-methoxy-1-cyclohexene, 1-ethoxy-1-cyclohexene and 1-methoxy-3,3,5-trimethylcyclohexene.

When —X— of Structure A is the diradical

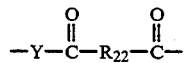

novel hydroxy-peroxyesters of Structure A can be prepared by reacting t-alkylperoxycarbonyl substituted acyl halides of Structure G

(G)

with di- or polyols or amino-alcohols of Structure H

(H)

Non-limiting examples of the t-alkylperoxycarbonyl substituted acyl halides of Structure G include 2-(t-butylperoxycarbonyl)benzoyl chloride, 2-(t-amylperoxycarbonyl)benzoyl chloride, 3-(t-butylperoxycarbonyl)propionyl chloride, 3-(t-amylperoxycarbonyl)propionyl chloride and 4-(t-butylperoxycarbonyl)butyryl chloride.

These t-alkylperoxycarbonyl substituted acyl halides can be prepared in a two-step synthetic scheme involving initially forming t-alkylperoxycarbonyl substituted carboxylic acids via reaction of t-alkyl hydroperoxides with cyclic anhydrides followed by reaction of the t-alkylperoxycarbonyl substituted carboxylic acids with acid chlorinating agents such as thionyl chloride.

Di- or polyols or amino-alcohols of Structure H include ethylene glycol, diethylene glycol, 1,2- and 1,3-propanediols, dipropylene glycol, 1,2-, 1,3- and 1,4-butanediols, 1,4-butynediol, 2,2-dimethyl-1,3-propanediol, 2-ethyl-1,3-hexanediol, 2,2,4-trimethyl-1,3-pentanediol, glycerol, trimethylolethane, trimethylolpropane, pentaerythritol, sorbitol, ethanolamine, diethanolamine, propanolamine, dipropanolamine, N-methylethanolamine and N-ethylethanolamine.

Novel Hydroxy-Peroxides

Representative hindered hydroxy-peroxyesters of this invention when —X— of Structure A is a direct bond include 3-hydroxy-1,1-dimethylpropyl peroxy-(2-chlorobenzoate), 3-hydroxy-1,1-dimethylbutyl peroxy-(2-methylbenzoate), 3-hydroxy-1,1-dimethylbutyl peroxy-(2,4-dimethylbenzoate), 3-hydroxy-1,1-dimethylbutyl peroxy-(2,6-dimethylbenzoate), 3-hydroxy-1,1-dimethylbutyl peroxy-(2-fluorobenzoate), 3-hydroxy-1,1-dimethylbutyl peroxy-(2-chlorobenzoate), 3-hydroxy-1,1-dimethylbutyl peroxy-(2-bromobenzoate), 3-hydroxy-1,1-dimethylbutyl peroxy-(2,4-dichlorobenzoate), 3-hydroxy-1,1-dimethylbutyl peroxy-(2-phenylbenzoate), 3-hydroxy-1,1-dimethylbutyl peroxy-(2-methoxybenzoate), 3-hydroxy-1,1-dimethylbutyl peroxy-(2-acetoxybenzoate).

Representative OO-hydroxyalkyl O-alkyl monoperoxydicarboxylates of this invention include OO-(3-hydroxy-1,1-dimethylbutyl) O-methyl monoperoxyphthalate, OO-(3-hydroxy-1,1-dimethylbutyl) O-n-butyl monoperoxyphthalate, OO-(3-hydroxy-1,1-dimethylbutyl) O-[(2,4-dioxacyclopentyl)methyl]monoperoxyphthalate (a), OO-(3-hydroxy-1,1-dimethylbutyl) O-[(3,3-dimethyl-2,4-dioxacyclopentyl)methyl]monoperoxyphthalate (b), OO-(3-hydroxy-1,1-dimethylbutyl) O-[(4,4-dimethyl-3,5-dioxacyclohexyl)methyl]monoperoxysuccinate (c), O-[(1,4,4-trimethyl-3,5-dioxacyclohexyl)methyl]monoperoxyglutarate (d), OO-(3-hydroxy-1,1-dimethylbutyl) O-(2,3-dihydroxypropyl) monoperoxyphthalate (e), OO-(3-hydroxy-1,1-dimethylbutyl) O-(1,3-dihydroxy-2-propyl)monoperoxysuccinate (f) and OO-(3-hydroxy-1,1-dimethylbutyl) O-(3-hydroxy-2-hydroxymethyl-2-methylpropyl) monoperoxyglutarate (g). Compositions (e), (f) and (g) are preparable by treating compositions (a) [or (b)], (c) and (d), respectively, with dilute aqueous mineral acid solution and isolating compositions (e), (f) and (g) by neutralizing with inorganic bases, separating off the neutralization salt and removing water by stripping in vacuo. Non-limiting examples of mineral acids useful for preparations of (e), (f) and (g) include HCl. HBr, $HNO_3$, $H_2SO_4$, $NaHSO_4$, $H_3PO_4$ and others. Non-limiting examples of inorganic bases useful for preparations of (e), (f) and (g) include KOH, NaOH, $Ca(OH)_2$, $NaHCO_3$, $Na_2CO_3$, $K_2CO_3$ and others.

Hydroxy-monoperoxycarbonates of this invention include OO-(3-hydroxy-1,1-dimethylpropyl) O-(2-ethylhexyl) monoperoxycarbonate, OO-(3-hydroxy-1,1-dimethylbutyl) O-isopropyl monoperoxycarbonate, OO-(3-hydroxy-1,1-dimethylbutyl) O-(2-butyl) monoperoxycarbonate, OO-(3-hydroxy-1,1-dimethylbutyl) O-(2-ethylhexyl) monoperoxycarbonate, OO-(3-hydroxy-1,1-dimethylbutyl) O-(2-butyloctyl) monoperoxycarbonate, OO-(3-hydroxy-1,1-dimethylbutyl) O-cyclohexyl monoperoxycarbonate, OO-(3-hydroxy-1,1-dimethylbutyl) O-cyclododecyl monoperoxycarbonate, OO-(3-hydroxy-1,1-dimethylbutyl) O-(4-t-butylcyclohexyl) monoperoxycarbonate, OO-(3-hydroxy-1,1-dimethylbutyl) O-(2,2,6,6-tetramethyl-4-piperidinyl) monoperoxycarbonate (and salts), OO-(3-hydroxy-1,1-dimethylbutyl) O-(1,2,2,6,6-pentamethyl-4-piperidinyl) monoperoxycarbonate (and salts), OO-(3-hydroxy-1,1-dimethylbutyl) O-(4,4-dimethyl-3,5-dioxacyclohexyl) monoperoxycarbonate (h), OO-(3-hydroxy-1,1dimethylbutyl) O-(3,5-dioxacyclohexyl) monoperoxycarbonate (i), OO-(3-hydroxy-1,1-dimethylbutyl) O-[(3,3-dimethyl-2,4-dioxacyclopentyl)methyl] monoperoxycarbonate (j) OO-(3-hydroxy-1,1-dimethylbutyl) O-[(2,4-dioxacyclopentyl)methyl] monoperoxycarbonate (k), OO-(3-hydroxy-1,1-dimethylbutyl) O-[(1,4,4-trimethyl-3,5-dioxacyclohexyl)methyl monoperoxycarbonate (1), OO-(3-hydroxy-1,1-dimethylbutyl) O-(2,3-dihydroxypropyl) monoperoxycarbonate (m), OO-(3-hydroxy-1,1-dimethylbutyl) O-(1,3-dihydroxy-2-propyl) monoperoxycarbonate (n) and OO-(3-hydroxy-1,1-dimethylbutyl) O-(3-hydroxy-2-hydroxymethyl-2-methylpropyl) monoperoxycarbonate (o). Compositions (m), (n) and (o) are preparable by treating compositions (h) [or (i)], (j) [or (k)] and (1), respectively, with dilute aqueous mineral acid solution and isolating compositions (m), (n) and (o) by neutralizing with inorganic bases, separating the neutralization salt and removing water by stripping in vacuo as described above.

Representative of hydroxy-monoperoxyketals of this invention include 2-methoxy-2-(3-hydroxy-1,1-dimethylpropylperoxy) propane, 2-methoxy-2-(3-hydroxy-1,1-dimethylbutylperoxy)propane and 1-methoxy-1-(3-hydroxy-1,1-dimethylbutylperoxy)cyclohexane.

When —X— of Structure A is the diradical

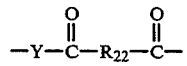

the novel hydroxy-peroxides of this invention include OO-t-amyl O-(2-hydroxyethyl)monoperoxyphthalate, OO-t-butyl O-(2-hydroxyethyl) monoperoxyphthalate, OO-t-butyl O-(2-hydroxypropyl) monoperoxyphthalate, OO-(1,1-dimethyl-2-propynyl) O-(2-hydroxypropyl) monoperoxyphthalate, OO-t-butyl O-(2-hydroxypropyl) monoperoxysuccinate, OO-t-butyl O-(2-hydroxypropyl) monoperoxyglutarate, OO-(1,1,3,3-tetramethybutyl), O-(2-hydroxypropyl) monoperoxyphthalate, OO-t-butyl, O-(2,3-dihydroxypropyl) monoperoxyphthalate, OO-t-butyl, O-(2,2-di[hydroxymethyl]propyl) monoperoxyphthalate, N-(2-hydroxyethyl) 2-(t-butylperoxycarbonyl)benzamide and N,N-di-(2-hydroxyethyl) 2-(t-butylperoxycarbonyl)benzamide.

Polymerization of Ethylenically Unsaturated Monomers

In the free-radical polymerizations of ethylenically unsaturated monomers at suitable temperatures and pressures the novel hydroxy-peroxides of Structure A of this invention are found to be efficient initiators (reduced initiator requirements, etc.). Ethylenically unsaturated monomers include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, methyl, ethyl, n-butyl, 2-hydroxyethyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate diethylene glycol bis(allyl carbonate) (i.e., ADC); acrolein; methyl vinyl ketone; or mixtures thereof.

Temperatures of 0° C.. to 250° C.., preferably 30° C.. to 200° C.., and hydroxy-peroxide levels (on a pure basis) of 0.002 to 3%, preferably 0.002 to 1% by weight based on monomer, are normally employed in conventional polymerizations and copolymerizations of ethylenically unsaturated monomers. The novel hydroxy-peroxides of this invention can be used in combination with other free-radical initiators such as peroxyesters which include t-butyl peroxypivalate, t-butyl peroxy-2-ethylhexanoate, t-butyl peroxyacetate, t-butyl peroxyneodecanoate, t-amyl peroxypivalate, t-amyl peroxyneodecanoate, 1,1,3,3-tetramethylbutyl peroxyneodecanoate, and α-cumyl peroxyneodecanoate; dialkyl peroxydicarbonates including di-n-propyl, diisopropyl, di-(sec-butyl), dicyclohexyl, di-(4-t-butylcyclohexyl), di-(2-phenoxyethyl), di-(2-ethylhexyl) and dihexadecyl peroxydicarbonates; acyl alkylsulfonyl peroxides including acetyl cyclohexylsulfonyl peroxide, and acetyl sec-heptylsulfonyl peroxide; diacyl peroxides including dibenzoyl peroxide, didodecyl peroxide, diisobutyryl peroxide and di-(2-methylpentanoyl)peroxide; diperoxyketals including 2,2-di-(t-butylperoxy)butane, 2,2-di-(t-butylperoxy)heptane, ethyl 3,3-di-(t-butylperoxy)butyrate, 1,1-di-(t-butylperoxy)-3,3,5-trimethylcyclohexane, 1,1-di-(t-butylperoxy)cyclohexane and 1,1-di-(t-amyl peroxy)cyclohexane; monoperoxycarbonates including OO-t-butyl O-isopropyl monoperoxycarbonate and OO-t-butyl O-(2-ethylhexyl) monoperoxycarbonate; dialkyl peroxides such as 2,5-dimethyl-2,5-di-(t-butylperoxy)hexane and azo compounds including azobis(isobutyronitrile), 2-t-butylazo-2-cyano-4-methoxy-4-methylpentane and 1-t-butylazo-1-cyanocyclohexane.

Using the hydroxy-peroxides of this invention in combination with these initiators adds flexibility to the processes of polymer producers and allows them to fine tune their polymerization processes.

Curing of Unsaturated Polyester Resins

In the curing of unsaturated resin compositions by heating at suitable curing temperatures in the presence of free-radical curing agents, the novel hydroxy-peroxides of Structure A of this invention exhibit enhanced curing activity in the curable unsaturated polyester resin compositions.

Unsaturated polyester resins that can be cured by the novel hydroxy-peroxides of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propanediols, 1,2-, 1,3-and 1,4-butanediols, 2,2-dimethyl-1,3-propanediol, 2-hydroxymethyl-2-methyl-1, 3-propanediol, 2-buten-1,4-diol, 2-butyn-1,4-diol, 2,4,4-trimethyl-1,3-pentanediol, glycerol, pentaerythritol, mannitol and others.

Mixtures of such di- or polyacids and/or mixtures of such di- or polyols may also be used. The di- or polycarboxylic acids may be partially replaced by saturated di-or polycarboxylic acids, such as adipic acid, succinic acid, sebacic acid and other, and/or by aromatic di- or polycarboxylic acids, such as phthalic acid, trimellitic acid, pyromellitic acid, isophthalic acid and terephthalic acid. The acids used may be substituted by groups such as halogen. Examples of such suitable halogenated acids are tetrachlorophthalic acid, tetrabromophthalic acid, 5,6-dicarboxy-1,2,3,4,7,7-hexachlorobicyclo(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others, or mixtures thereof, which are copolymerizable with said unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid) as well as the monomer component, styrene. Other types of unsaturated polyester resin compositions can be cured using the novel hydroxy-peroxides of this invention as curing catalysts. These resins, called unsaturated vinyl ester resins, consist of a vinyl ester resin portion and one or more polymerizable monomer components. The vinyl ester resin component can be made by reacting a chloroepoxide, such as epichlorohydrin, with appropriate amounts of a bisphenol such as Bisphenol A [2,2-di-(4-hydroxyphenyl)propane], in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C.. to 200° C.. and hydroxy-peroxide levels of about 0.05% to 5% or more by weight of curable unsaturated polyester resin composition are normally employed for curing of the unsaturated polyester resins.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

Curing of Elastomers and Crosslinking of Thermoplastic Polymers

In the curing of elastomeric compositions, and the crosslinking of polymer compositions, by heating at suitable curing and crosslinking temperatures in the presence of free-radical curing and crosslinking agents, the novel hydroxy-peroxides of this invention exhibit curing and crosslinking activities.

Elastomeric resin compositions that can be cured by the novel hydroxy-peroxides of this invention include elastomers such as ethylene-propylene copolymers (EPR), ethylene-propylene-diene terpolymers (EPDM), polybutadiene (PBD), silicone rubber (SR), nitrile rubber (NR), neoprene, fluoroelastomers and ethylene-vinyl acetate copolymer (EVA).

Polymer compositions that can be crosslinked by the hydroxy-peroxides of this invention include olefin thermoplastics such as chlorinated polyethylene (CPE), low density polyethylene (LDPE), linear-low density polyethylene (LLDPE), and high density polyethylene (HDPE).

Temperatures of about 80° C. to 310° C. and hydroxy-peroxide levels of about 0.1% to 10%, preferably 0.5% to 5%, based on weight of curable elastomeric resin composition or crosslinkable olefin polymer composition, are normally employed.

The curable elastomeric resin composition or crosslinkable polymer composition can be optionally filled with the materials listed above for use with the conventional unsaturated polyester resin compositions.

Modification of Propylene Homopolymers and Copolymers

In the processes for modifying propylene homopolymers, and, propylene copolymers (e.g., beneficial degradation of polypropylene (PP) by reducing the polymer molecular weight and the polymer molecular weight distribution), the novel hydroxy-peroxides of this invention exhibit polypropylene modification activity.

Temperatures of about 140° C.. to 340° C.. and hydroxy-peroxide levels of about 0.01% to 1.0% based on weight of modifiable polyolefins or copolymers are normally employed. Optionally, up to 1% by weight of molecular oxygen can be employed as a modification co-catalyst.

EXAMPLES

EXAMPLE 1

Preparation of OO-(3-Hydroxy-1,1-dimethylbutyl) O-(2-Ethylhexyl) Monoperoxycarbonate (I-1)

A jacketed reactor equipped with a stirrer, a thermometer and an addition funnel was charged with 40 mL of methylene chloride, 25.1 g (0.14 mole) of 74.9% 3-hydroxy-1,1-dimethylbutyl hydroperoxide and 39.2 g (0.14 mole) of 20% aqueous KOH solution and the mixture was stirred at 20° C. The liquid phases were allowed to separate and the lower methylene chloride layer was removed. Then another 40 mL of methylene chloride was added, the mixture stirred at 20° C.., the liquid layers settled and the lower methylene chloride layer removed. Then the vigorously stirred aqueous solution was heated to 45° C.. and to it, added rapidly over 4.5 minutes, was 19.3 g (0.10 mole) of 99% 2-ethylhexyl chloroformate and the resulting mixture was stirred for an additional 45 minutes at 45° C.. The resulting vigorously stirred two phase liquid mixture was cooled to 20° C. and to it was added 80 mL of pentane and 50 mL of water. Stirring was stopped and the lower aqueous layer was removed and discarded. The pentane solution was then washed at 20° C. with 50 mL portions of 10% aqueous KOH solution and then twice with 50 mL portions of water. The pentane solution was then dried over 10% by weight of anhydrous MgSO$_4$. After separation of the spent desiccant by filtration, the pentane was removed in vacuo leaving 24.3 g (83.8% of theory, uncorrected) of a clear, colorless liquid. An infrared spectrum of the product showed a strong OH band at ca. 3410 cm−1, an unresolved double carbonyl band at ca. 1710 cm−1 and 1735 cm−1 and a small —OO— band at ca. 830 cm−1. These IR spectral bands corresponded to the desired structure and confirmed that the product was the title product. The product had an Act[O] content of 4.71%. Based on a theoretical Act[O] of 5.51% for the desired title product, the assay was 85.5% and the corrected yield was 71.6%.

EXAMPLE 2

Preparation of OO-(3-Hydroxy-1,1-dimethylbutyl) O-(2-Butyl) Monoperoxycarbonate (I-2)

A jacketed reactor equipped with a stirrer, a thermometer and an addition funnel was charged with 30 mL of methylene chloride, 16.6 g (0.093 mole) of 75.2% 3-hydroxy-1,1-dimethylbutyl hydroperoxide and 26.0 g (0.093 mole) of 20% aqueous KOH solution and the mixture was stirred at 20° C.. for 5 minutes. The liquid phases were allowed to separate and the lower methylene chloride layer was removed. Then another 30 mL of methylene chloride was added, the mixture stirred at 20° C., the liquid layers settled and the lower methylene chloride layer removed. Then the vigorously stirred aqueous solution was heated to 40°–45° C. and to it, added rapidly over 2.0 minutes, was 5.5 g (0. 040 mole) of 99% 2-butyl chloroformate and the resulting mixture was stirred for an additional 25 minutes at 40°–45° C. The resulting vigorously stirred two phase liquid mixture was cooled to 20°–25° C.. and to it was added 50 mL of pentane. Stirring was stopped and the lower aqueous layer was removed and discarded. The pentane solution was then washed twice at 20° C.. with 50 mL portions of 10% aqueous KOH solution and then three times with 70 mL portions of water. The pentane solution was then dried over 10% by weight of anhydrous MgSO$_4$. After separation of the spent desiccant by filtration, the pentane was removed in vacuo leaving 3.9 g (41.5% of theory, uncorrected) of a clear, colorless liquid. An infrared spectrum of the product showed a strong OH band at ca. 3410 cm−1, an unresolved double carbonyl band at ca. 1705 cm−1 and 1735 cm−1 and an —OO— band at ca. 865 cm−1. These IR spectral bands corresponded to the desired structure and confirmed that the product was the title product. The product had an Act[O] content of 6.05%. Based on a theoretical Act[O] of 6.83% for the desired title product, the assay was 88.6% and the corrected yield was 36.8%

EXAMPLE 3

Preparation of OO-(3-Hydroxy-1,1-dimethylbutyl) O-Isopropyl Monoperoxycarbonate (I-3)

A jacketed reactor equipped with a stirrer, a thermometer and an addition funnel was charged with 30 mL of methylene chloride, 25.0 g (0.14 mole) of 75% 3-hydroxy-1,1-dimethylbutyl hydroperoxide and 39.2 g (0.14 mole) of 20% aqueous KOH solution and the mixture was stirred at ca. 25° C.. for 3 minutes. The liquid phases were allowed to separate and the lower methylene chloride layer was removed. Then another 30 mL of methylene chloride wash was employed and the spent methylene chloride layer was settled, separated and discarded. Then the vigorously stirred aqueous solution was heated to ca. 42°–48° C.. and to it, added rapidly over ca. 5 minutes, was 7.4 g (0.060 mole) of 98% isopropyl chloroformate and the resulting mixture was stirred for an additional 35 minutes at 45° C.. after which 50 mL of water was added. The resulting vigorously stirred two phase liquid mixture was cooled to 20°–25° C.. and to it was added 50 mL of pentane. Stirring was stopped and the lower aqueous layer was removed and discarded. The pentane solution was then washed twice at 20° C.. with 50 mL portions of 10% aqueous KOH solution and then washed to a pH of ca. 7 with 100 mL portions of water. The pentane solution was then dried over 10% by weight of anhydrous $MgSO_4$. After separation of the spent desiccant by filtration, the pentane was removed in vacuo leaving 7.4 g (56.1% of theory, uncorrected) of a liquid product. An infrared spectrum of the product showed a strong OH band at ca. 3400 cm−1, a strong carbonyl band at ca. 1730 cm−1 (a shoulder at 1780 cm−1) and an —OO— bandit ca. 880 cm−1. These IR spectral bands corresponded to the expected IR spectrum of the desired structure and confirmed that the product was the title product. The product had an Act[O] content of 6.65%. Based on a theoretical Act[O] of 7.26% for the desired title product, the assay was 91.6% and the corrected yield was 51.4%.

EXAMPLE 4

Preparation of OO-(3-Hydroxy-1,1-dimethylbutyl) O-Cyclohexyl Monoperoxycarbonate (I-4)

The apparatus and the procedure employed in Example 3 was used in this example. Reactants employed were 75% 3-hydroxy-1,1-dimethylbutyl hydroperoxide (25.0 g; 0.14 mol 20% aqueous KOH solution (39.2 g; 0.114 mole) and 97.2% cyclohexyl chloroformate (10.0 g; 0.06 mole). After the usual work-up, 11.8 g (75.6% of theory, uncorrected) of a liquid product was obtained. An infrared spectrum of the product showed a strong OH band at ca. 3400 cm−1, an unresolved double carbonyl band at ca. 1700 cm−1 and 1720 cm−1 and a small —OO— band at ca. 835 cm−1. These IR spectral bands corresponded to the desired structure and confirmed that the product was the title product. The product had an Act[O] content of 5.45%. Based on a theoretical Act[O] of 6.15% for the desired title product, the assay was 88.6% and the corrected yield was 67.0%.

EXAMPLE 5

Preparation of OO-(3-Hydroxy-1,1-dimethylbutyl) O-(2,2,6,6-Tetramethyl-4-piperidinyl) Monoperoxycarbonate (I-5)

An Erlenmeyer flask was charged with 14.9 g (0.12 mole) of 45% aqueous KOH solution and 20 mL of water. The flask contents were cooled to 15° C.. and 12.4 g (0.0694 mole) of 74.9% 3-hydroxy-1,1-dimethylbutyl hydroperoxide was slowly added and allowed to stir for 5 minutes. The flask contents were then transferred to a separatory funnel and were washed with 25 mL of methylene chloride (poor separation) and with 15 mL of methyl t-butyl ether (better separation). The aqueous layer was then transferred to a 3-neck round bottom flask and cooled to 10° C. Then 0.2 g of N,N-dimethylaminopyridine (DMAP) was added and the solution stirred. To this vigorously stirred solution at 10°–15° C.. was slowly added 8.9 g (0.0315 mole) of 2,2,6,6-tetramethyl-4-chlorocarbonyloxypiperidinium chloride over a period of about 30 minutes, however, the latter reactant did not dissolve readily, therefore, 30 mL of tetrahydrofuran (THF) was added. This appeared to facilitate the reaction. The reaction mixture was then stirred for an additional 30 minutes at 10°–15° C., then for 120 minutes at 20°–25° C. Then 100 mL of methylene chloride was added, stirred and separated. A second wash was carried out with a 50 mL portion of methylene chloride. The combined methylene chloride washes were then washed with 50 mL of 5% aqueous NaOH solution, with 50 mL of water, three times with 50 mL portions of saturated aqueous $NaHSO_3$ solution and once with 50 mL of 5% aqueous $NaHCO_3$ solution. The methylene chloride solution was then dried over 10% by weight of anhydrous $MgSO_4$. After separation of the spent desiccant by filtration, the solvent was removed in vacuo leaving 7.6 g (76% of theory, uncorrected) of white crystals, mp, 119°–27° C.. The product had an Act[O] content of 4.47% and a 3-hydroxy-1,1-dimethylbutyl hydroperoxide content of 1.67%. Based on a theoretical Act[O] of 7.26% for the desired title product and correcting for the Act[O] due to 3-hydroxy-1,1-dimethylbutyl hydroperoxide, the assay of the product was 84.9% and the corrected yield was 64.5%.

EXAMPLE 6

Preparation of OO-(3-Hydroxy-1,1-dimethylbutyl) O-(2-Phenoxyethyl) Monoperoxycarbonate (I-6)

The apparatus and the procedure employed in Example 3 was used in this example. Reactants employed were 75% 3-hydroxy-1,1-dimethylbutyl hydroperoxide (25.0 g; 0.14 mole), 20% aqueous KOH solution (39.2 g; 0.14 mole) and 99% 2-phenoxyethyl chloroformate (12.2 g; 0.06 mole). After the usual work-up, 11.8 g (65.9% of theory, uncorrected) of a straw-color liquid product was obtained. An infrared spectrum of the product showed an OH band at ca. 3380 cm−1, a strong carbonyl band at ca. 1730 cm−1 and a small —OO— band at ca. 890 cm−1. The product had an Act[O] content of 2.65%.

EXAMPLE 7

Preparation of 3-Hydroxy-1,1-dimethylbutyl Peroxy-(2-methylbenzoate) (I-7)

A jacketed reactor equipped with a stirrer, a thermometer and an addition funnel was charged with 19.8 g (0.110 mole) of 74.4% 3-hydroxy-1,1-dimethylbutyl hydroperoxide and 30.9 g (0.110 mole) of 20% aqueous KOH solution at 15° C.. The resulting solution was washed twice with 40 g portions of toluene and twice with 40 mL portions of pentane. Then 25 g of water and 50 mL of pentane were added to the aqueous solution and the solution was cooled to 0°–5° C.. Then to the vigorously stirred reaction mass at 0°–5° C.. was added a solution of 7.7 g (0.050 mole) of 100% 2-methylbenzoyl chloride and 50 mL of pentane over a period of 5 minutes. The resulting mixture was stirred for an additional 15 minutes at 0°–5° C. after which stirring was stopped and the reaction mass was allowed to separate into liquid phases. The lower aqueous layer was removed and discarded. The pentane solution was then washed twice at 10° C. with 40 g portions of 10% aqueous KOH solution and then twice with 20 g portions of saturated aqueous NaHCO$_3$. All during the work-up a pentane insoluble organic layer was carried along. This layer was dissolved in 50 mL of methylene chloride, dried over anhydrous MgSO$_4$ and, after separation of the spent desiccant by filtration, the methylene chloride was removed in vacuo leaving 6.1 g (48% of theory, uncorrected) of a clear, colorless oil. The pentane solution was then dried over 10% by weight of anhydrous MgSO$_4$. After separation of the spent desiccant by filtration, the pentane was removed in vacuo leaving 3.1 g (25% of theory, uncorrected) of a clear, colorless liquid. Infrared spectra of the two products showed that the two were identical, therefore, they were combined. An infrared spectrum of the combined product showed a strong OH band at ca. 3475 cm−1, a very strong peroxyester carbonyl band at ca. 1740 cm−1 and an —OO— band at ca. 820 cm−1. No ester band was observed at about 1700 cm−1, hence, no ester-peroxyester was present in the product. The product had an Act[O] content of 6.28%. Based on a theoretical Act[O] of 6.34% for the desired title product, the assay was 99.5% and the corrected yield was 72.7%. The half-life of I-7 at 100° C. in alpha-methylstyrene (0.20 molar in I-7) was found to be 4.05 hours, therefore, the 10 hour half-life temperature for I-7 was estimated to be about 94° C. t-Butyl peroxy-(2-methylbenzoate), a commercial peroxyester similar to I-7, was found to have a 100° C.. half-life in benzene (0.20 molar) of 8.7 hours and a 10 hour half-life temperature of about 99° C. Therefore, I-7 was significantly more active than was t-butyl peroxy-(2-methylbenzoate) based on decomposition data.

EXAMPLE 8

Preparation of 3-Hydroxy-1,1-dimethylbutyl Peroxy-(2-chlorobenzoate) (I-8)

A jacketed reactor equipped with a stirrer, a thermometer and an addition funnel was charged with 20.1 g (0.110 mole) of 73.4% 3-hydroxy-1,1-dimethylbutyl hydroperoxide and 30.9 g (0.110 mole) of 20% aqueous KOH solution at 15° C.. The resulting solution was washed twice with 40 g portions of methylene chloride. Then 25 g of water and 50 mL of methylene chloride were added to the aqueous solution and the solution was cooled to 0°–5° C. To the vigorously stirred reaction mass at 0°–5° C. was added a solution of 9.2 g (0.050 mole) of 95% 2-chlorobenzoyl chloride and 50 mL of methylene chloride over a period of 5 minutes. The resulting mixture was stirred for an additional 20 minutes at 0°–5° C. after which stirring was stopped and the reaction mass was allowed to separate into liquid phases. The upper aqueous layer was removed and discarded. The methylene chloride solution was then washed twice at 10° C. with 40 g portions of 10% aqueous KOH solution and then twice with 40 g portions of saturated aqueous NaHCO$_3$. The methylene chloride solution was then dried over anhydrous MgSO$_4$, and, after separation of the spent desiccant by filtration, the methylene chloride was removed in vacuo leaving 11.8 g (86.7% of theory, uncorrected) of a clear, colorless liquid. An infrared spectrum of the product showed a strong OH band at ca. 3480 cm−1 and a very strong peroxyester carbonyl band at ca. 1740 cm−1. No ester band was observed at about 1700 cm−1, hence, no ester-peroxyester was present in the product. The product had an Act[O] content of 5.23%. Based on a theoretical Act[O] of 5.87% for the desired title product, the assay was 89.1% and the corrected yield was 77.2%.

EXAMPLE 9

Preparation of 3-Hydroxy-1,1-dimethylbutyl Peroxy-(2-bromobenzoate) (I-9)

The same process and work-up procedure as used in Example 8 was employed in this example. Reacted at 15° C.. were 20.1 g (0.110 mole) of 73.4% 3-hydroxy-1,1-dimethylbutyl hydroperoxide, 30.9 g (0.110 mole) of 20% aqueous KOH solution, 25 g of water and 11.2 g (0.05 mole) of 98% 2-bromobenzoyl chloride. Obtained after the work-up was 14.8 g (93.1% of theory, uncorrected) of a clear, colorless liquid. An infrared spectrum of the product showed a strong OH band at ca. 3480 cm−1 and a very strong peroxyester carbonyl band at ca. 1740 cm−1. No ester band was observed at about 1700 cm−1, hence, no ester-peroxyester was present in the product. The product had an Act[O]content of 4.41%. Based on a theoretical Act[O] of 5.04% for the desired title product, the assay was 87.5% and the corrected yield was 81.5%.

EXAMPLE 10

Preparation of 3-Hydroxy-1,1-dimethylbutyl Peroxy-(2-acetoxybenzoate) (I-10)

The same process and work-up procedure as used in Example 8 was employed in this example. Reacted at 15° C.. were 20.1 g (0.110 mole) of 73.4% 3-hydroxy-1,1-dimethylbutyl hydroperoxide, 65.0 g (0.115 mole) of 10% aqueous KOH solution and 10.1 g (0.05 mole) of ca. 98% 2-acetoxybenzoyl chloride. Obtained after the work-up was 4.6 g (31% of theory, uncorrected) of a clear, yellow liquid. An infrared spectrum of the product showed a strong OH band at ca. 3400 cm−1, a very strong peroxyester carbonyl band at ca. 1730 cm−1 and an ester carbonyl band at about 1700 cm−1. The ester band observed at about 1700 cm−1 was due to the acetoxy group in the desired product.

EXAMPLE 11

Reaction of 3-Hydroxy-1,1-dimethylbutyl Hydroperoxide with Benzoyl Chloride

A jacketed reactor equipped with a stirrer, a thermometer and an addition funnel was charged with 29.7 g (0.20 mole) of 90.3% 3-hydroxy-1,1-dimethylbutyl hydroperoxide and 44.0 g (0.22 mole) of 20% aqueous NaOH solution at 20°–25° C. To the vigorously stirred reaction mass at 25°–30° C.. was slowly added a solution of 14.1 g (0.10 mole) of 100% benzoyl chloride over a period of 20 minutes. The resulting mixture was stirred for an additional 180 minutes at 25°–30° C. after which 50 mL of water and 100 mL of methylene chloride were added. Stirring was stopped and the reaction mass was allowed to separate into liquid phases. The lower aqueous layer was removed and discarded. The organic solution was then washed once with 25 mL of water, once with about 25 mL of buffered Na$_2$SO$_3$ solution (i.e., 22 g of water, 1.5 g of sodium acetate, 1.0 g of acetic acid and 0.63 g of sodium sulfite) and once with 25 mL of 7.7% aqueous NaHCO$_3$ solution. All washes were carried out at 20°–25° C.. The methylene chloride solution was then dried over 10% by weight of anhydrous MgSO$_4$. After separation of the spent desiccant by filtration, the solvent was removed in vacuo leaving 17.5 g (73.5% of theory, uncorrected) of a liquid product. The product had a peroxyester Act[O] content of 3.76%. The product obtained in this example was 3-benzoyloxy-1,1-dimethylbutyl peroxybenzoate (C-1a). The assay of C-1a was 80.5% and the corrected yield was 82.4%. C-1a is the benzoate-peroxybenzoate disclosed in Example 3 of U.S. Pat. No. 3,236,872 (Ref. 1). This reference teaches that reactions of benzoyl chlorides and acetyl chloride with 3-hydroxy-1,1-dimethylbutyl hydroperoxide results in formation of ester-peroxyesters. In the instant example the skewing of the process conditions in favor of formation of 3-hydroxy-1,1-dimethylbutyl peroxybenzoate (C-1, a hydroxyalkyl peroxybenzoate), by employing excess 3-hydroxy-1,1-dimethylbutyl hydroperoxide failed to result in formation of C-1, but instead, C-1a was formed. Contrary to the above finding, we surprisingly and unexpectedly found that, under essentially the same process conditions as employed in Example 11, hindered benzoyl chlorides, such as 2-chlorobenzoyl chloride, 2-methylbenzoyl chloride, 2-bromobenzoyl chloride and 2-acetoxybenzoyl chloride, resulted in formation of the corresponding hydroxyalkyl substituted peroxybenzoates (see Compositions I-7, I-8, I-9 and I-10, Examples 7, 8, 9 and 10). These results are tabulated in the table below.

| REACTION PRODUCTS FROM REACTION OF BENZOYL CHLORIDES WITH 3-HYDROXY-1,1-DIMETHYLBUTYL HYDROPEROXIDE | | | | |
|---|---|---|---|---|
| Example | Product | Type (1) Product | Type of Benzoyl Chloride | Assay % |
| 7 | I-7 | H-P | Hindered (2-methyl) | 99.5 |
| 8 | I-8 | H-P | Hindered (2-chloro) | 89.1 |
| 9 | I-9 | H-P | Hindered (2-bromo) | 87.5 |
| 10 | I-10 | H-P | Hindered (2-acetoxy) | — |
| 11 | C-1a | E-P | Non-Hindered | 80.5 |

(1) H-P—Hydroxy-Peroxyester
E-P—Ester-Peroxyester

EXAMPLE 12

Preparation OO-t-Butyl O-(2-Hydroxypropyl) Monoperoxyphthalate (I-11)

A 300 mL 3-neck round-bottom flask, equipped with a magnetic stirrer, a thermometer, a cold water condenser and an addition funnel, was charged with 100 mL of methyl t-butyl ether, 16.7 g (0.06 mole) of 91.3% of 2-(t-butylperoxycarbonyl)benzoyl chloride and 5.5 g (0.07 mole) of pyridine. To this vigorously stirred solution at 20° C.. was added 22.8 g (0.30 mole) of 1,2-propanediol over a period of 20 minutes. During the addition there was a slight exotherm and a white precipitate formed. The reaction mass was warmed to 25° C.. and stirred at 25° C.. for 240 minutes. The precipitate was separated by filtration and the white solid was washed with about 25 mL of methyl t-butyl ether. The methyl t-butyl ether washings were combined with the filtrate and the filtrate was washed twice with 50 mL portions of 5% aqueous HCl solution, then twice with 50 mL portions of 3% aqueous NaHCO$_3$ solution. The methyl t-butyl ether solution was then dried over 10% by weight of anhydrous MgSO$_4$ and, after separation of the spent desiccant by filtration, the solvent was removed in vacuo leaving 17.4 g (98.3% of theory, uncorrected) of a straw-color liquid. An infrared spectrum of the product showed a strong OH band at ca. 3500 cm−1 and two carbonyl bands at ca. 1720 cm−1 and 1770 cm−1. The product had a peroxyester Act[O] content of 5.02%. Based on a theoretical Act[O] of 5.40% for the desired title product, the assay was 93.0% and the corrected yield was 91.4%.

EXAMPLE 13

Preparation of OO-t-Butyl O-(2-Hydroxypropyl) Monoperoxysuccinate (I-12)

A 250 mL 3-neck round-bottom flask, equipped with a magnetic stirrer, a thermometer, a cold water condenser and an addition funnel, was charged with 50 mL of methylene chloride, 4.2 g (0.052 mole) of pyridine and 19.0 g (0.25 mole) of 1,2-propanediol. The resulting vigorously stirred solution was cooled to 10° C.. and to it was slowly added a solution of 11.5 g (0.050 mole) of 94% 3-(t-butylperoxycarbonyl)propionyl chloride in 10 mL of methylene chloride over a period of 20 minutes. The reaction mass was warmed to 20° C.. and stirred at 20° C.. for 210 minutes. The reaction mixture was washed at 10°–15° C.. with 50 mL of aqueous 5% HCl solution and then twice with 100 mL portions of 5% aqueous NaHCO$_3$ solution. The methylene chloride solution was then dried over 10% by weight of anhydrous MgSO$_4$ and, after separation of the spent desiccant by filtration, the solvent was removed in vacuo leaving 12.4 g (100% of theory, uncorrected) of a straw-color liquid. An infrared spectrum of the product showed a strong OH band, a strong and broad carbonyl band at ca. 1720–1780 cm−1 and a strong —OO— band at ca. 850 cm−1. The product had a peroxyester Act[O] content of 6.29%. Based on a theoretical Act[O] of 6.45% for the desired title product, the assay was 97.5% and the corrected yield was 97.5%.

EXAMPLE 14

Preparation of 2-Methoxy-2-(3-hydroxy-1,1-dimethylbutylperoxy)propane (I-13)

A 250 mL 3-neck round-bottom flask, equipped with a magnetic stirrer, a thermometer, a cold water condenser and an addition funnel, was charged with 100 mL of methylene chloride and 3.6 g (0.050 mole) of methyl isopropenyl ether. To this solution at 20°–5° C.. was slowly added 8.0 g (0.053 mole) of dry, 88.4% 3-hydroxy-1,1-dimethylbutyl hydroperoxide over a period of about 30 minutes. The reaction mass was warmed to 35° C.. and stirred at 35° C.. for 150–180 minutes. The reaction mass was washed twice with 50 mL portions of water. The methylene chloride solution was then dried over 10% by weight of anhydrous MgSO$_4$ and, after separation of the spent desiccant by filtration, the solvent was removed in vacuo leaving 9.2 g (89.3% of theory, uncorrected) of a liquid product. An infrared spectrum of the product showed a strong OH band at ca. 3500 cm−1 and a small —OO— band at ca. 870 cm−1. The product had an Act[O] content of 8.32%. Based on a theoretical Act[O] of 7.76% for the desired title product, the assay was 100% and the corrected yield was 89.3%.

EXAMPLE 15

Preparation of OO-(3-Hydroxy-1,1-dimethylbutyl) O-(2,4-Dioxacyclopentyl)methyl Monoperoxycarbonate (I-14)

In this example the chloroformate of glycerol formal was initially synthesized by treating glycerol formal (a mixture of [2,4-dioxacyclopentyl]methanol and 3,5-dioxacyclohexanol) with excess phosgene followed by isolation of the product, a mixture of (2,4-dioxacyclopentyl)methyl chloroformate and 3,5-dioxacyclohexyl chloroformate. For the sake of brevity the chloroformate mixture was referred to as (2,4-dioxacyclopentyl)methyl chloroformate. Subsequently, (2,4-dioxacyclopentyl)methyl chloroformate was reacted with 3-hydroxy-1,1-dimethylbutyl hydroperoxide in the presence of aqueous KOH solution to form the product, a mixture of OO-(3-hydroxy-1,1-dimethylbutyl) O-(2,4-dioxacyclopentyl)methyl monoperoxycarbonate and OO-(3-hydroxy-1,1-dimethylbutyl) O-(3,5-dioxacyclohexyl) monoperoxycarbonate (I-14). Again, for the sake of brevity, the product of this example was referred to as OO-(3-hydroxy-1,1-dimethylbutyl) O-(2,4-dioxacyclopentyl) methyl monoperoxycarbonate rather than the two-component mixture name.

A jacketed reactor equipped with a stirrer, a thermometer and an addition funnel was charged with 80 mL of methyl t-butyl ether, 47.8 g (0.26 mole) of 73.4% 3-hydroxy-1,1-dimethylbutyl hydroperoxide and 145 g (0.26 mole) of 10% aqueous KOH solution and the mixture was stirred at 20° C.. The liquid phases were allowed to separate and the lower methyl t-butyl ether layer was removed. Then another 80 mL of methyl t-butyl ether was added, the mixture stirred at 20° C., the liquid layers settled and the lower methyl t-butyl ether layer removed. This wash procedure was repeated a third time. Then the vigorously stirred aqueous solution was heated to 24°-28° C. and to it was slowly added (over 45 minutes) 59.2 g (0.30 mole) of 98% (2,4-dioxacyclopentyl)methyl chloroformate and the resulting mixture was stirred for an additional 90 minutes at 25°-30° C.. Then 300 mL of methyl t-butyl ether was added, stirring was terminated and the lower aqueous layer was separated from the organic phase and discarded. The product solution was then washed at 20° C.. twice with 100 g portions of 10% aqueous KOH solution, then several times with 100 mL portions of water in order to adjust the pH to about 7. The methyl t-butyl ether solution was then dried over 10% by weight of anhydrous MgSO4. After separation of the spent desiccant by filtration, the methyl t-butyl ether was removed in vacuo leaving 7.2 g (14% of theory, uncorrected) of a light, straw-colored liquid. An infrared spectrum of the product showed a strong OH band at ca. 3400 cm−1, an unresolved double carbonyl band at ca. 1790 cm−1 and 1740 cm−1 and a small —OO— band at ca. 840 cm−1. The product contained 1.7% 3-hydroxy-1,1-dimethylbutyl hydroperoxide and had a monoperoxycarbonate Act[O] content of 4.99%. Based on a theoretical Act[O] of 6.05% for the desired title product mixture, the assay was 82.5% and the corrected yield was 11.2%.

EXAMPLE 16

Preparation of OO-(3-Hydroxy-1,1-dimethylbutyl) O-(3,3-Dimethyl-2,4-dioxacyclopentyl)methyl Monoperoxycarbonate (I-15)

In this example the chloroformate of solketal was initially synthesized by treating solketal (a mixture of [3,3-dimethyl-2,4-dioxacyclopentyl]methanol and 4,4-dimethyl-3,5-dioxacyclohexanol) with excess phosgene followed by isolation of the product, a mixture of (3,3-dimethyl-2,4-dioxacyclopentyl)methyl chloroformate and 4,4-dimethyl-3,5-dioxacyclohexyl chloroformate. For the sake of brevity the chloroformate mixture was referred to as (3,3-dimethyl-2,4-dioxacyclopentyl)methyl chloroformate. Subsequently, (3,3-dimethyl-2,4-dioxacyclopentyl)methyl chloroformate was reacted with 3-hydroxy-1,1-dimethylbutyl hydroperoxide in the presence of aqueous KOH solution to form the product, a mixture of OO-(3-hydroxy-1,1-dimethylbutyl) O-(3,3-dimethyl-2,4-dioxacyclopentyl)methyl monoperoxycarbonate and OO-(3-hydroxy-1,1-dimethylbutyl) O-(4,4-dimethyl-3,5-dioxacyclohexyl) monoperoxycarbonate (I-15). Again, for the sake of brevity, the product of this example was referred to as OO-(3-hydroxy-1,1-dimethylbutyl) O-(3,3-dimethyl-2,4-dioxacyclopentyl)methyl monoperoxycarbonate rather than the two-component mixture name.

A jacketed reactor equipped with a stirrer, a thermometer and an addition funnel was charged with 50 mL of methylene chloride, 25.6 g (0.14 mole) of 73.4% 3-hydroxy-1,1-dimethylbutyl hydroperoxide and 62.7 g (0.14 mole) of 12.5% aqueous KOH solution and the mixture was stirred at 20°-25° C. The liquid phases were allowed to separate and the lower methylene chloride layer was removed. Then another 50 mL of methylene chloride was added, the mixture stirred at 20°-25° C.., the liquid layers settled and the lower methylene chloride layer was removed. Then the vigorously stirred aqueous solution was heated to 23°-28° C.. and to it over 20 minutes was slowly added 19.7 g (0.10 mole) of 98.7% (3,3-dimethyl-2,4-dioxacyclopentyl)methyl chloroformate and the resulting mixture was stirred for an additional 90 minutes at 25° C.. Then 100 mL of methyl t-butyl ether was added, stirring was terminated and the lower aqueous layer was separated from the organic phase and discarded. The product solution was then washed at 20° C.. twice with 50 g portions of 10% aqueous KOH solution, then several times with 50 mL portions of water in order to adjust the pH to about 7. The methyl t-butyl ether solution was then dried over 10% by weight of anhydrous MgSO4. After separation of the spent desiccant by filtration, the methyl t-butyl ether was removed in vacuo leaving 13.0 g (44% of theory, uncorrected) of a colorless liquid. An infrared spectrum of the product showed a strong OH band at ca. 3390 cm−1, an unresolved double carbonyl band at ca. 1790 cm−1 and 1745 cm−1 and a small —OO— band at ca. 835 cm−1. The product contained 0.2% 3-hydroxy-1,1-dimethylbutyl hydroperoxide and had a monoperoxycarbonate Act[O] content of 5.27%. Based on a theoretical Act[O] of 5.47% for the desired title product mixture, the assay was 96.3% and the corrected yield was 42.7%.

EXAMPLE 17

Preparation of OO-(3-Hydroxy-1,1-dimethylbutyl) O-(2,3-Dihydroxypropyl) Monoperoxycarbonate (I-16)

In this example the product mixture of Example 16, i.e., I-15, a mixture of OO-(3-hydroxy-1,1-dimethylbutyl) O-(3,3-dimethyl-2,4-dioxacyclopentyl)methyl monoperoxycarbonate and OO-(3-hydroxy-1,1-dimethylbutyl) O-(4,4-dimethyl-3,5-dioxacyclohexyl) monoperoxycarbonate, was treated with dilute aqueous hydrochloric acid solution to form the desired product mixture, I-16, consisting of OO-(3-hydroxy-1,1-dimethylbutyl) O-(2,3-dihydroxypropyl) monoperoxycarbonate and OO-(3-hydroxy-1,1-dimethylbutyl) O-(1,3-dihydroxy-2-propyl) monoperoxycarbonate. For the sake of brevity, the product of this example was referred to as OO-(3-hydroxy-1,1-dimethylbutyl) O-(2,3-dihydroxypropyl) monoperoxycarbonate rather than the two-component mixture name.

A flask equipped with a magnetic stirrer and a thermometer was charged with 5.0 g (0.0165 mole) of 96.3% OO-(3-hydroxy-1,1-dimethylbutyl) O-(3,3-dimethyl-2,4-dioxacyclopentyl)methyl monoperoxycarbonate (I-15) and 5.0 g (0.0068 mole) of 5% aqueous hydrochloric acid solution at 20°–25° C.. The resulting mixture was stirred at 20°–25° C.. for 240 minutes. Then excess solid sodium carbonate (ca. 1.0 g) was added in order to neutralize the hydrochloric acid. About 150 mL of acetone was added to the neutralized reaction mass and the solid sodium salts that formed (NaCl and $Na_2CO_3$) were separated by filtration. The acetone and water were removed in vacuo at room temperature. While the acetone and water were being removed, additional inorganic sodium salts precipitated and had to be removed by filtration. Obtained was 4.0 g (96% of theory, uncorrected) of a colorless liquid. An infrared spectrum of the product showed a strong and broad OH band at ca. 3400 cm−1, an unresolved double carbonyl band at ca. 1775 cm−1 and 1740 cm−1 and a small —OO— band at ca. 830 cm−1. The OH band at 3400 cm−1 for the product of this example (I-16) was significantly broader and deeper than the OH band at 3390 cm−1 for the starting material, I-15. In addition, the IR spectra of the starting material (I-15) and the product (I-16) were significantly different in the 700–1500 cm−1 spectral region. The product contained 8.4% 3-hydroxy-1,1-dimethylbutyl hydroperoxide and had a monoperoxycarbonate Act[O] content of 4.74%. Based on a theoretical Act[O] of 6.34% for the desired title product mixture, the assay was 74.8% and the corrected yield was 71.9%. The IR spectral data and the Act [O] data confirmed that the product obtained in this example was the desired title product mixture, I-16.

EXAMPLE 18

SPI Exotherms of Hydroxy-Peroxides

The unsaturated polyester resin composition employed in this example was a mixture of an unsaturated polyester and styrene monomer. The unsaturated polyester was an alkyd resin made by esterifying the following components:.

| Component | Quantity (moles) |
|---|---|
| Maleic Anhydride | 1.0 moles |
| Phthalic Anhydride | 1.0 moles |
| Propylene Glycol | 2.2 moles |

To the resulting resin was added 0.013% by weight of hydroquinone inhibitor. The alkyd resin had an Acid No. of 45–50. Seven (7) parts by weight of the above unsaturated polyester alkyd was diluted with three (3) parts by weight of monomeric styrene. The resulting unsaturated polyester resin composition had the following properties:
a. Viscosity (Brookfield No. 2 at 20 r.p.m.): 13.0 poise
b. Specific gravity: 1.14

CURING PROCEDURE

Gelation and cure characteristics of the initiator tested were determined using a conventional SPI Exotherm Procedure ("SUGGESTED SPI PROCEDURE—Procedure for Running Exotherm Curves—Using Thermocouple Needle, 24th Annual Technical Conference, 1969, Reinforced Plastics/Composites Division, the Society of the Plastics Industry, Inc., page 6").

Using the procedure at 138° C.. (280° F.) OO-(3-hydroxy-1,1-dimethylbutyl) O-isopropyl monoperoxycarbonate (I-3), a hydroxy-monoperoxycarbonate of the instant invention, and OO-t-butyl O-(2-ethylhexyl) monoperoxycarbonate (A-1), a monoperoxycarbonate of the art, were evaluated. The results are summarized in Table 15-1 and show that I-3, a composition of the instant invention was active in gelling and curing the unsaturated polyester resin.

TABLE 18-1

| | SPI Exotherm Data at 138° C. | | | | |
|---|---|---|---|---|---|
| Curing Catalyst | Level, % | Gel, mins | Cure, mins | Peak Exotherm, °F. | Barcol Hardness |
| A-1 | 0.75 | 1.9 | 2.6 | 450 | 40–45 |
| I-3 | 0.72 (1) | 2.2 | 3.0 | 459 | 35–40 |

(1) Equivalent Act[O] level to that of 0.75 phr of A-1

Also, OO-t-butyl O-(2-hydroxypropyl) monoperoxyphthalate (I-11), a hydroxy-peroxyester of the instant invention, and t-butyl peroxybenzoate (A-2), a peroxyester of the art, were evaluated using this procedure. The temperature employed was 100° C.. (212° F.). The results are summarized in Table 15-2 and show that I-11, a composition of the instant invention, was active in gelling and curing the unsaturated polyester resin.

TABLE 18-2

| | SPI Exotherm Data at 100° C. | | | | |
|---|---|---|---|---|---|
| Curing Catalyst | Level, % | Gel, mins | Cure, mins | Peak Exotherm, °F. | Barcol Hardness |
| A-2 | 1.0 | 8.0 | 10.5 | 390 | 50 |
| I-11 | 1.0 | 9.4 | 13.7 | 364 | 45–50 |

Also evaluated using the procedure were 3-hydroxy-1,1-dimethylbutyl peroxy-(2-methylbenzoate) (I-7), a hydroxy-peroxyester of the instant invention, and t-butyl peroxybenzoate (A-2), a peroxyester of the art. The temperature employed was 115° C.. (239° F.). The results are summarized in Table 15-3 and show that I-7, a composition of the instant invention, was surprisingly more active in gelling and curing the unsaturated polyester resin than was A-2, a peroxyester of the art.

TABLE 18-3

| | SPI Exotherm Data at 115° C. | | | | |
|---|---|---|---|---|---|
| Curing Catalyst | Level, % | Gel, mins | Cure, mins | Peak Exotherm, °F. | Barcol Hardness |
| A-2 | 1.0 | 4.4 | 5.5 | 436 | 40–45 |
| I-7 | 1.0 | 2.3 | 3.3 | 436 | 40–45 |
| I-7 | 1.3 (1) | 2.0 | 2.8 | 413 | 40–45 |

(1) Equivalent Act[O] level to that of 1.0 phr of A-2

What is claimed: .
1. In a process of polymerizing ethylenically unsaturated monomers comprising adding to the reaction mass of said monomers an initiating amount of a peroxide, the improvement comprising the use in such process of hydroxy peroxides having the structure A:

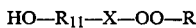  (A)

and wherein:
I. When X is a direct bond:
R is selected from the structures:

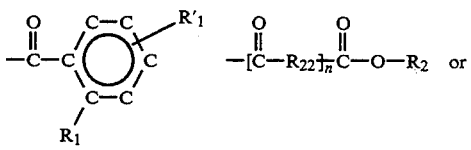 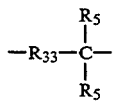 or

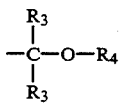

wherein:

R₁ is a lower alkyl radical of 1 to 4 carbons, an alkoxy radical of 1 to 4 carbons, a phenyl radical, an acyloxy radical of 2 to 8 carbons, a t-alkylperoxycarbonyl radical of 5 to 9 carbons, hydroxy, fluoro, chloro or bromo, R'₁ is H or is selected from the same radicals as R₁, and may be the same as or different than R₁; n is 0 or 1;

R₂ is a substituted or unsubstituted alkyl radical of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6–10 carbons, hydroxy, chloro, bromo or cyano; R₂ is a substituted or unsubstituted cycloalkyl radical of 5 to 12 carbons, a substituted or unsubstituted 4-piperidinyl radical, or a substituted or unsubstituted 1,3-dioxan-5-yl radical with substituents for the cycloalkyl, piperidinyl or dioxanyl radicals being one or more lower alkyl radicals of 1 to 4 carbons; or R₂ is the radical:

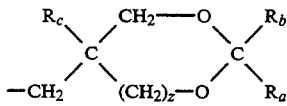

wherein z is 0 or 1, $R_a$, $R_b$ and $R_c$ are the same or different and are H- or alkyl radicals of 1 to 8 carbons, or $R_a$ and $R_b$ can be connected forming together with the carbon atoms to which they are attached a substituted or unsubstituted ring containing 5-12 carbons, substituents being one or more alkyl radicals of 1 to 5 carbons or phenyl radicals;

R₂₂ is a substituted or unsubstituted alkylene diradical of 2 to 3 carbons, substituents being one or more lower alkyl radicals of 1 to 4 carbons, or a substituted or unsubstituted 1,2-phenylene diradical, substituents being one or more lower alkyl radicals of 1 to 4 carbons, chloro, bromo, nitro or carboxy;

R₃ is a lower alkyl radical of 1 to 4 carbons, or the two R₃ radicals can be connected together forming together with the carbon atom to which they are attached a ring containing 5 to 6 carbons;

R₄ is a lower alkyl radical of 1 to 4 carbons; the R₁₁ diradical is the structure,

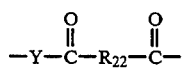

wherein R₅ is a lower alkyl radical of 1 to 4 carbons; and

R₃₃ is a substituted or unsubstituted alkylene diradical of 2 to 4 carbons, substituents being one or more lower alkyl radicals of 1 to 4 carbons, with the proviso that when n is 0 and R₃₃ is an alkylene diradical of 2 carbon atoms substituted with methyl on the C atom alpha to the hydroxy group, R₂ is not an unsubstituted alkyl radical of 1 to 9 carbon atoms or an alkyl radical of 1 to 9 carbon atoms substituted with one or more lower alkyl radicals of 1 to 6 carbon atoms; and II. when X is the diradical:

$$-Y-\overset{O}{\underset{\|}{C}}-R_{22}-\overset{O}{\underset{\|}{C}}-$$

Y is oxy or —NR₆—, wherein R₆ is H or a substituted or unsubstituted alkyl radical of 1 to 8 carbons, substituents being one or more lower alkyl radicals of 1 to 4 carbons or hydroxy, and R₂₂ is as defined above;

R is a substituted or unsubstituted t-alkyl radical of 4 to 12 carbons, a cumyl radical or a cumyl radical substituted with lower alkyl radicals said lower alkyl radicals totaling 1 to 4 carbon atoms, substituents for the t-alkyl radical being lower alkyl radicals of 1 to 4 carbons or a t-alkylperoxy radical of 4 to 8 carbons; and R₁₁ is a substituted or unsubstituted alkylene diradical of 2 to 8 carbons, substituents being one or more lower alkyl radicals of 1 to 4 carbons, lower hydroxyalkyl radicals of 1 to 4 carbons or hydroxy.

2. The process of claim 1 wherein the ethylenically unsaturated monomer is styrene or ethylene.

* * * * *